United States Patent
Maa et al.

(10) Patent No.: US 10,874,762 B2
(45) Date of Patent: Dec. 29, 2020

(54) AIR-FILTERING ANTI-BACTERIAL LIGHTING APPARATUS

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 102 days.

(21) Appl. No.: 16/180,416

(22) Filed: Nov. 5, 2018

(65) Prior Publication Data

US 2020/0139000 A1    May 7, 2020

(51) Int. Cl.
| | |
|---|---|
| *A61L 9/20* | (2006.01) |
| *B01J 35/00* | (2006.01) |
| *B01J 21/06* | (2006.01) |
| *B01J 23/50* | (2006.01) |
| *B01J 23/52* | (2006.01) |

(52) U.S. Cl.
CPC ............. *A61L 9/205* (2013.01); *B01J 21/063* (2013.01); *B01J 23/50* (2013.01); *B01J 23/52* (2013.01); *B01J 35/004* (2013.01); *B01J 35/0013* (2013.01); *A61L 2209/12* (2013.01); *A61L 2209/14* (2013.01)

(58) Field of Classification Search
CPC .. A61L 9/205; A61L 2209/12; A61L 2209/24; A61L 2202/25; B01J 35/004; B01J 35/0013; B01J 21/063; B01J 23/50; B01J 23/52
See application file for complete search history.

(56) References Cited

U.S. PATENT DOCUMENTS

| | | |
|---|---|---|
| 6,242,752 B1 | 6/2001 | Soma et al. |
| 9,522,384 B2 | 12/2016 | Lu et al. |
| 10,118,170 B1 | 11/2018 | Maa et al. |
| 2012/0275960 A1* | 11/2012 | Seck ................. A61L 9/205 422/121 |
| 2017/0266335 A1* | 9/2017 | Al-Zeer ............. A61L 9/205 |

\* cited by examiner

*Primary Examiner* — Lessanework Seifu
(74) *Attorney, Agent, or Firm* — Han IP PLLC; Andy M. Han

(57) ABSTRACT

An anti-bacterial lighting apparatus includes one translucent housing, at least one light source, and an air circulation mechanism. The translucent housing is air permeable, has as least one air inflow port, and has an anti-bacterial photocatalytic film on its inside surface. The at least one light source is inside the housing, and its light activates the anti-bacterial photocatalytic film on the housing. The air circulation mechanism, such as a fan, is at the air inflow port of the housing. It sucks the ambient air from outside the housing and forces the air through the air-permeable housing. The air-permeable housing traps airborne bacteria and viruses, and the activated anti-bacterial photocatalytic film kills the trapped bacteria and viruses. Moreover, the light shines through the translucent housing while the apparatus is filtering the air and killing the airborne bacteria and viruses.

13 Claims, 4 Drawing Sheets

AIR-FILTERING ANTI-BACTERIAL LIGHTING APPARATUS

BACKGROUND

Technical Field

The present disclosure pertains to the field of lighting devices and, more specifically, proposes an anti-bacterial lighting apparatus.

Description of Related Art

Photocatalysts are known to become active under ultraviolet light and kill bacteria by breaking down the cell wall of the bacteria. Soma, R., et al., in U.S. Pat. No. 6,242,752 teaches the use of a photocatalytic film made of anatase-type titanium dioxide ($TiO_2$) on the lens of a lighting device such that, as the light originating from the lighting device shines through the titanium oxide film, the UV rays of the light activate the photocatalyst, causing it to break down the bacteria cell wall and resulting in the killing of the bacteria. In U.S. Pat. No. 9,522,384, Liu L. et al. teaches the use of rhombus-shape anatase-type titanium dioxide ($TiO_2$) such that this new type of $TiO_2$ can be activated by visible light wavelengths and become germicidal active.

In U.S. Pat. No. 10,118,170, Maa C. et al. (hereinafter "Maa") teaches an anti-bacterial lighting apparatus where the photocatalytic film is coated on the surface of the lens of the apparatus, and as the light of the light source of the apparatus activates the photocatalytic film on the lens, the photocatalytic film will kill any airborne bacteria or viruses making physical contact with the lens. The limitation with Maa's teaching is that for the airborne bacteria or viruses to make physical contact with photocatalytic film, it requires air movement to bring the airborne bacteria or viruses to the lens. If there isn't sufficient air movement where the lighting apparatus is installed, then the germicidal effect is limited.

The present disclosure introduces a new anti-bacterial lighting apparatus that overcomes the limitation of the lighting apparatus taught by Maa C. et al. in U.S. Pat. No. 10,118,170 through the use a built-in air circulation mechanism for bringing airborne bacteria and viruses to the surface of a translucent housing that is coated with photocatalytic film. Moreover, the translucent housing is air-permeable and thus functions as an air filter. As the air passes through the housing, the airborne bacteria and viruses are filtered and trapped on the surface of the housing and are killed by the photocatalytic film. As a result, the new anti-bacterial lighting apparatus enhances greatly the filtering and killing of airborne bacteria and viruses.

SUMMARY

In one aspect, the lighting apparatus comprises one translucent housing, at least one light source, and an air circulation mechanism. The translucent housing may be air permeable, and it contains at least one air inflow port. The inside surface of the translucent housing is coated with anti-bacterial photocatalytic film. The at least one lighting is inside the housing. The light originated from the light source shines through the translucent housing, thus illuminating the area around the apparatus. The light also activates the anti-bacterial photocatalytic film on the housing so that it would kill bacteria and viruses making contact with it. The air circulation mechanism is at the air inflow port of the housing. It sucks the ambient air from outside the housing and forces the air through air-permeable housing. As the air passing through, the air-permeable housing traps airborne bacteria and viruses, and the activated anti-bacterial photocatalytic film begins to kill the trapped bacteria and viruses. Moreover, the translucent housing also serves as a lens cover for the light of the light source to shine through it, while the apparatus is filtering the air and killing the airborne bacteria and viruses. So this apparatus is an air-filtering anti-bacterial lighting device.

In some embodiments, the main active ingredient of the anti-bacterial photocatalytic film is titanium dioxide ($TiO_2$). In some other embodiments the main active ingredient is rhombus-shape anatase-type titanium dioxide ($TiO_2$). As shown in U.S. Pat. No. 9,522,384 by Liu L. et al that rhombus-shape anatase-type titanium dioxide has a much higher volume density than the sphere-shape anatase-type titanium dioxide, thus it is more effective in the photocatalytic killing of bacteria and viruses.

In some embodiments, the anti-bacterial photocatalytic film may contain at least one other active metal ingredient such as but not limited to, silver, gold, copper, zinc, nickel, or any combination thereof. These metals when embedded in the photocatalyst are known to enhance the photocatalytic activity with visible light. Some photocatalytic film may contain more than one type of metals for a better photocatalytic effectiveness.

The titanium dioxide is classified as a semiconducting photocatalyst. Recently technology breakthrough has demonstrated that noble metal nanoparticles such as gold (Au) and silver (Ag) can are a class of efficient photocatalysts working by mechanisms distinct from those of semiconducting photocatalysts (https://pubs.rsc.org/en/content/article-landing/2013/gc/c3gc40450a#!divAbstract). The present disclosure is not limited to the use of semiconducting photocatalysts. In some embodiments, the main active ingredient of the anti-bacterial photocatalytic film is a noble metal nanoparticle such as but not limited to, gold (Au) or sliver (Ag).

In some embodiments, at least 95% of the spectral power distribution (SPD) of the at least one light source is in a visible light wavelength range greater than 400 nm. In other words, the light source is not required to be a UV light source. The present disclosure only requires a regular light source emitting primarily the visible wavelengths.

There is no restriction on the shape of the translucent housing. Cylindrical shape is common where one opening of the cylinder holds the air circulation mechanism and the other opening of the cylinder is capped off with a cover or a control panel. In some embodiments, the housing may take the form of a rectangular prism, a pyramid, a cone, a cube, a sphere, and other three dimensional shape.

In some embodiments, the air circulation mechanism is a fan. It is foreseeable to have more than one fans in order to increase the airflow.

In some embodiments, the outside surface of the housing is also coated with anti-bacterial photocatalytic film. This has the benefit of killing the airborne bacteria and viruses that makes the contact with the outside surface of the housing.

In some embodiments, the housing surface may contain multiple folds. This has the effect of increasing the overall surface area for housing, and thus enhancing the air filtering efficiency and the photocatalytic killing of airborne bacteria and viruses.

In some embodiments, the housing surface may have more than one air-permeable layers, where one layer may be for anti-bacterial photocatalytic coating, another layer for odor removal, and perhaps one other layer for PM 2.5 nano-particle filtering.

Since the housing functions as an air filter, the dust will get stuck on the housing surface and gradually blocks the physical contact of the anti-bacterial photocatalytic film with the airborne bacteria and viruses, thus reducing the anti-microbial effectiveness of the apparatus. And the housing will become dirty over time. To overcome this issue, in some embodiments, the housing of the present disclosure is replaceable. Some embodiments may even has a timer on usage of the housing or a sensor detecting the cleanness of the housing so as to remind the user to replace the housing when necessary.

In some embodiment, the housing may be made of non-woven fabric. There are at least three advantages of using non-woven fabric as the material for air filter. Firstly, it is easier to control the air permeation rate through the manufacturing process of the non-woven air filter. Secondly, it is easier to apply the anti-bacterial photocatalytic film on a non-woven fabric because it has plenty of spores for absorbing the photocatalytic particles. Thirdly, the overall production cost is low with non-woven fabric air filter.

BRIEF DESCRIPTION OF THE DRAWINGS

The accompanying drawings are included to aid further understanding of the present disclosure, and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting apparatuses having different form factors.

The present disclosure discloses an anti-bacterial lighting apparatus that has one translucent housing, at least one light source, and an air circulation mechanism. The translucent housing is air permeable, has as least one air inflow port, and has an anti-bacterial photocatalytic film on its inside surface. The at least one light source is inside the housing, and its light activates the anti-bacterial photocatalytic film on the housing. The air circulation mechanism, such as a fan, is at the air inflow port of the housing. It sucks the ambient air from outside the housing and forces the air through the air-permeable housing. The air-permeable housing traps airborne bacteria and viruses, and the activated anti-bacterial photocatalytic film kills the trapped bacteria and viruses. Moreover, the light shines through the translucent housing while the apparatus is filtering the air and killing the airborne bacteria and viruses.

Example Implementations

Figure 1:
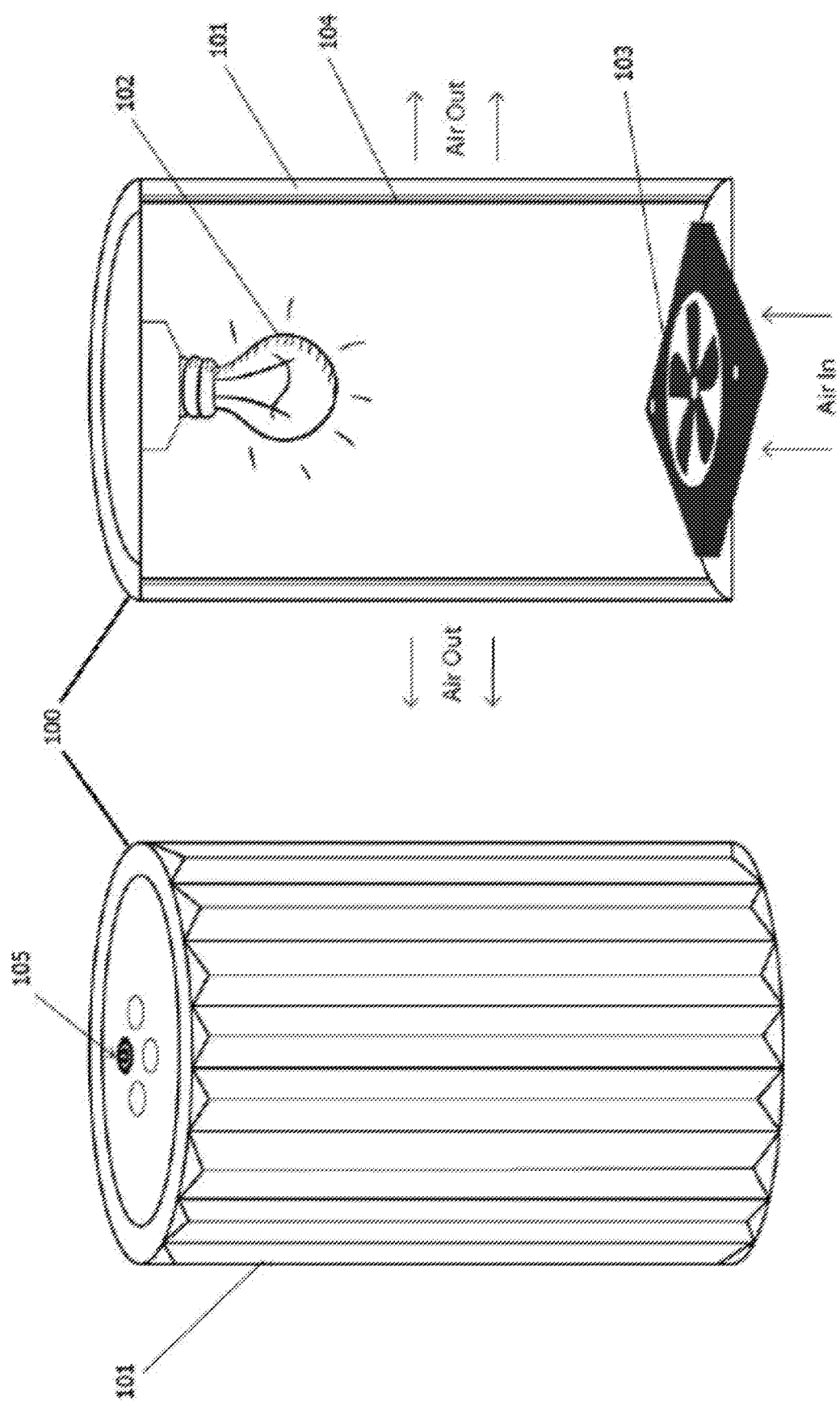
FIG. 1 schematically depicts a diagram of anti-bacterial lighting fixture with a cylindrical housing.

FIG. 1 is an embodiment of the lighting apparatus of the present disclosure in a form of a cylindrical lighting fixture 100. The light source 102 is a light bulb and resides inside the translucent housing 101. The air circulation mechanism is a fan 103 located at one end of the cylindrical shape housing 101. The other end of the housing is covered with a control panel 105 for turning on and off the light and the fan. The inside surface of the housing 101 is coated with anti-bacterial photocatalytic film 104. The ambient air is pulled into the housing through the fan 103 and then passes through the photocatalytic film 104 and the air-permeable housing 101. The airborne bacteria and viruses are trapped by the air-permeable housing 101 and killed by the photocatalytic film 104. The air-permeable housing 101 has a folding surface for increasing the overall surface area and efficiency of air filtering. The air-permeable housing is made of non-woven fabric so that it can be coated effectively with photocatalytic film without affecting its air permeation rate. Though not shown explicitly in the figure, the control panel 105 can be removed for replacing the light bulb and the air permeable housing 101.

Figure 2:
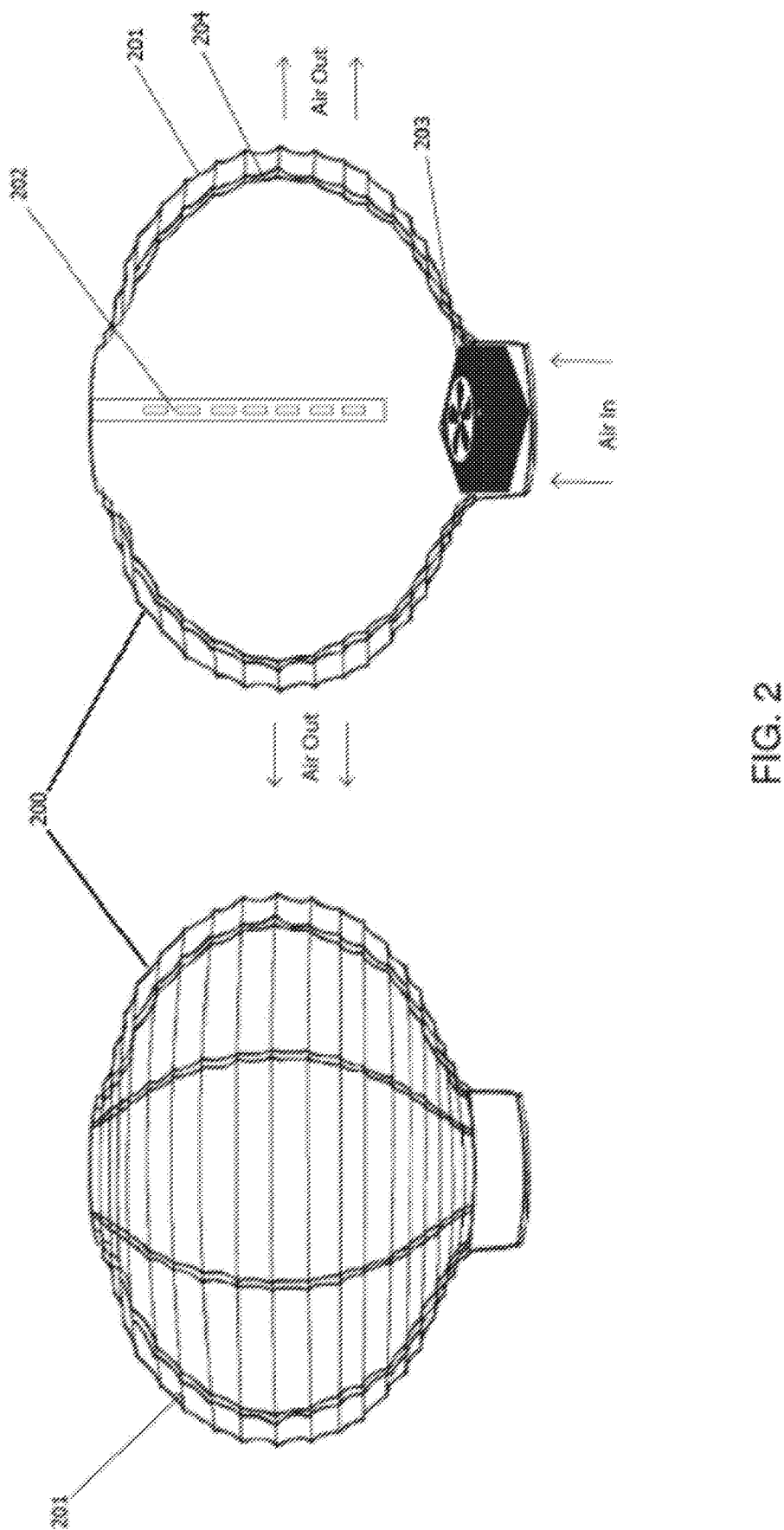
FIG. 2 schematically depicts the cross section view of the anti-bacterial lighting fixture with a sphere housing.

FIG. 2 is another embodiment of the lighting apparatus of the present disclosure in the form for a sphere lighting fixture 200. The light source 202 is an LED light source and resides inside the translucent housing 201. The air circulation mechanism is a fan 203 located at the bottom of the housing 201. The inside surface of the housing 201 is coated with anti-bacterial photocatalytic film 204. The ambient air is pulled into the housing through the fan 203 and then passes through the photocatalytic film 204 and the air-permeable housing 201. The air-permeable housing 201 has a folding surface. On top of the fixture 200, there is a hook 205 used for hanging the fixture. Though not shown explicitly in the figure, the housing 201 can be removed for replacement when it becomes dirty.

Figure 3:
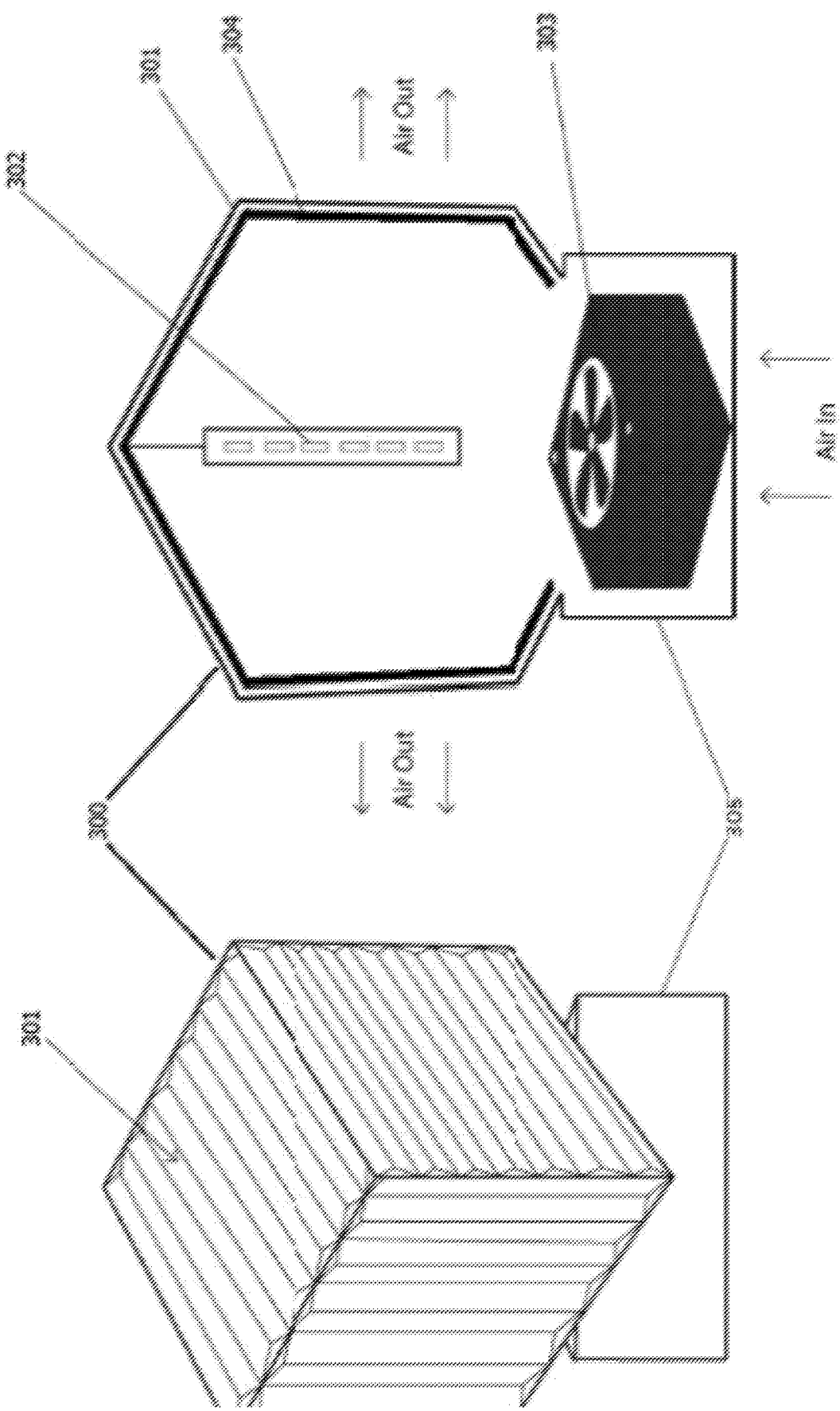
FIG. 3 schematically depicts a diagram of anti-bacterial lighting fixture with a cubic housing.

FIG. 3 is another embodiment of the lighting apparatus of the present disclosure in the form for a cubical lighting fixture 300. The light source 302 is an LED light source and resides inside the translucent housing 301. The air circulation mechanism is a fan 303 located at the bottom of the housing 301 and inside a base stand 305. The inside surface of the housing 301 is coated with anti-bacterial photocatalytic film 304. The ambient air is pulled into the housing through the fan 203 and then passes through the photocatalytic film 304 and the air-permeable housing 301. The air-permeable housing 301 has a folding surface. The base stand 305 enables this cubical lighting fixture to be used as a free standing fixture. Though not shown explicitly in the figure, the housing 301 is replaceable.

Figure 4:
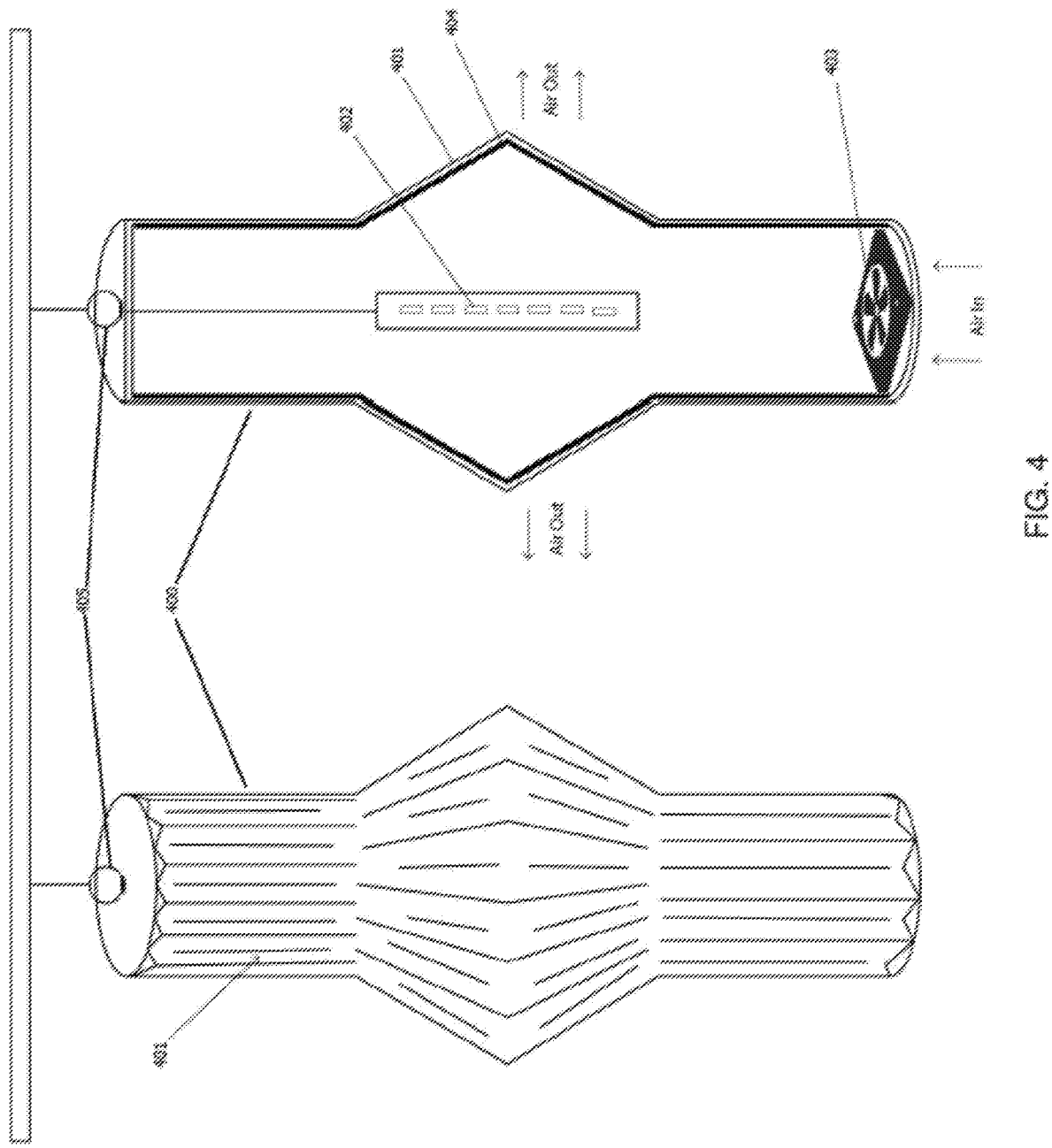
FIG. 4 schematically depicts a diagram of anti-bacterial lighting fixture with an irregular housing.

FIG. 4 is another embodiment of the lighting apparatus of the present disclosure in the form for an irregular elongated lighting fixture 400. The light source 402 is an elongated LED light source and resides inside the translucent housing 401. The elongated light source lights up the elongated housing 401 evenly. The air circulation mechanism is a fan 403 located at the bottom of the housing 401 and inside a base stand 405. The inside surface of the housing 401 is coated with anti-bacterial photocatalytic film 404. The ambient air is pulled into the housing through the fan 403 and then passes through the photocatalytic film 404 and the air-permeable housing 401. The air-permeable housing 401 has a folding surface. On top of this embodiment is a hanging mechanism, as shown in the figure a hook 405, for hanging the light fixture. Though not shown explicitly in the figure, the housing 401 is replaceable.

Additional and Alternative Implementation Notes

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A lighting apparatus, comprising:
   one translucent housing;
   at least one light source; and
   an air circulation mechanism,
   wherein:
      the translucent housing is free-standing and requiring no frame to house the at least one light source and the air circulation mechanism,
      the translucent housing is air permeable, contains at least one air inflow port, and is coated with an anti-bacterial photocatalytic film on its inside surface,
      the at least one light source is disposed inside the housing, and its light shines through the translucent housing and activates the anti-bacterial photocatalytic film on the housing,
      the air circulation mechanism is disposed at the air inflow port of the housing, sucks an ambient air from outside the housing, and forces the air through the air-permeable housing, and
      the translucent housing traps airborne bacteria and viruses, and the activated anti-bacterial photocatalytic film kills the trapped bacteria and viruses.

2. The lighting apparatus of claim 1, wherein a main active ingredient of the anti-bacterial photocatalytic film is titanium dioxide ($TiO_2$).

3. The lighting apparatus of claim 2, wherein the main active ingredient is rhombus-shaped anatase-type titanium dioxide ($TiO_2$).

4. The lighting apparatus of claim 1, wherein the anti-bacterial photocatalytic film contains at least one other active metal ingredient comprising silver, gold, copper, zinc, nickel, or a combination thereof.

5. The lighting apparatus of claim 1, wherein a main active ingredient of the anti-bacterial photocatalytic film is a noble metal nanoparticle comprising gold (Au) or sliver (Ag).

6. The lighting apparatus of claim 1, wherein at least 95% of a spectral power distribution (SPD) of the at least one light source is in a visible light wavelength range greater than 400 nm.

7. The lighting apparatus of claim 1, wherein a shaped of the translucent housing is cylindrical, rectangular column, pyramidal, cubical, or spherical.

8. The lighting apparatus of claim 1, wherein the air circulation mechanism comprises a fan.

9. The lighting apparatus of claim 1, wherein an outside surface of the housing is coated with another anti-bacterial photocatalytic film.

10. The lighting apparatus of claim 1, wherein a surface of the housing contains multiple folds.

11. The lighting apparatus of claim 1, wherein a surface of the housing has more than one air-permeable layers.

12. The lighting apparatus of claim 1, wherein the housing is replaceable.

13. The lighting apparatus of claim 1, wherein the housing is non-woven fabric.

\* \* \* \* \*